US012005021B2

United States Patent
Smith et al.

(10) Patent No.: US 12,005,021 B2
(45) Date of Patent: Jun. 11, 2024

(54) HAPTIC ACTUATORS AND THEIR METHODS OF USE

(71) Applicant: EMBR Labs IP LLC, Boston, MA (US)

(72) Inventors: Matthew J. Smith, Somerville, MA (US); David Cohen-Tanugi, Somerville, MA (US); Kristen Warren, Cambridge, MA (US); Robert Balke, Winchester, MA (US)

(73) Assignee: EMBR Labs IP LLC, Boston, MA (US)

( * ) Notice: Subject to any disclaimer, the term of this patent is extended or adjusted under 35 U.S.C. 154(b) by 41 days.

(21) Appl. No.: 16/129,182

(22) Filed: Sep. 12, 2018

(65) Prior Publication Data

US 2019/0110950 A1 Apr. 18, 2019

Related U.S. Application Data

(60) Provisional application No. 62/571,311, filed on Oct. 12, 2017.

(51) Int. Cl.
*A61H 23/00* (2006.01)
*A61F 7/00* (2006.01)
(Continued)

(52) U.S. Cl.
CPC .......... *A61H 23/02* (2013.01); *A61F 7/00* (2013.01); *A61F 7/007* (2013.01); *G06F 1/163* (2013.01);
(Continued)

(58) Field of Classification Search
None
See application file for complete search history.

(56) References Cited

U.S. PATENT DOCUMENTS 2,314,423 A   3/1943   Page
4,585,002 A   4/1986   Kissin
(Continued)

FOREIGN PATENT DOCUMENTS

CA   2627021 A1   10/2009
CN   101048194 A   10/2007
(Continued)

OTHER PUBLICATIONS

[No Author Listed] Poster for Wristify: Thermal comfort, reimagined. MIT Department of Materials Science and Engineering, Mad Mec. Oct. 15, 2013, 1 page.
(Continued)

*Primary Examiner* — Bradley H Philips
*Assistant Examiner* — Savannah L Gabriel
(74) *Attorney, Agent, or Firm* — Wolf, Greenfield & Sacks, P.C.

(57) ABSTRACT

Methods of operating a haptic actuator to apply physical and/or thermal sensations to a user to provide subjective symptom relief to a user are described. In some embodiments, a haptic actuator may be automatically activated when one or more detected user states are compared to one or more predetermined activation parameters to determine the user is experiencing an episode related to a condition of the user. In another embodiment, one or more operating parameters of a haptic actuator may be updated if the haptic actuator did not provided a desired amount of subjective symptom relief to a user during use. In yet another embodiment, a haptic actuator may create an event log based on activation events when the haptic actuator is used to provide symptom relief for a condition of the user.

20 Claims, 3 Drawing Sheets

(51) Int. Cl.
  *A61H 23/02* (2006.01)
  *G06F 1/16* (2006.01)
  *G06F 3/01* (2006.01)
  *G06F 3/0346* (2013.01)
  *G16H 20/30* (2018.01)
  *G16H 40/63* (2018.01)
  *G16H 40/67* (2018.01)
  *G16H 50/20* (2018.01)
  *A61F 7/02* (2006.01)

(52) U.S. Cl.
  CPC .............. *G06F 3/011* (2013.01); *G06F 3/016* (2013.01); *G06F 3/017* (2013.01); *G06F 3/0346* (2013.01); *G16H 20/30* (2018.01); *G16H 40/63* (2018.01); *G16H 40/67* (2018.01); *G16H 50/20* (2018.01); *A61F 2007/0009* (2013.01); *A61F 2007/0019* (2013.01); *A61F 2007/0029* (2013.01); *A61F 2007/0035* (2013.01); *A61F 2007/0039* (2013.01); *A61F 2007/0044* (2013.01); *A61F 2007/0093* (2013.01); *A61F 2007/0228* (2013.01); *A61F 2007/0233* (2013.01); *A61F 2007/0234* (2013.01); *A61F 2007/0236* (2013.01); *A61H 2201/02* (2013.01); *A61H 2201/501* (2013.01); *A61H 2230/655* (2013.01); *G06F 2203/011* (2013.01)

(56) References Cited

U.S. PATENT DOCUMENTS

| | | | |
|---|---|---|---|
| 4,860,748 A * | 8/1989 | Chiurco | A61F 7/007 607/96 |
| 5,169,384 A * | 12/1992 | Bosniak | A61F 7/007 604/20 |
| 5,746,702 A | 5/1998 | Gelfgat et al. | |
| 5,956,963 A * | 9/1999 | Lerner | F25D 5/02 62/530 |
| 7,713,295 B2 | 5/2010 | Ahn et al. | |
| 7,871,427 B2 | 1/2011 | Dunbar et al. | |
| 8,083,786 B2 | 12/2011 | Gafni et al. | |
| 8,267,983 B2 | 9/2012 | Rogers et al. | |
| 8,397,518 B1 | 3/2013 | Vistakula | |
| 8,658,943 B1 * | 2/2014 | Larsen | A61F 7/007 607/108 |
| 9,849,024 B2 | 12/2017 | Mandel | |
| D830,874 S | 10/2018 | Shames et al. | |
| 10,182,937 B2 | 1/2019 | Smith et al. | |
| 10,878,691 B1 * | 12/2020 | McLendon | G16H 50/20 |
| 2007/0193278 A1 | 8/2007 | Polacek et al. | |
| 2008/0086063 A1 | 4/2008 | Baxter et al. | |
| 2010/0198322 A1 * | 8/2010 | Joseph | A61F 7/007 607/108 |
| 2010/0204764 A1 * | 8/2010 | Garetz | A61F 7/10 607/104 |
| 2012/0089063 A1 | 4/2012 | Olson et al. | |
| 2013/0036549 A1 * | 2/2013 | McKlarney | A61M 19/00 5/413 R |
| 2013/0116503 A1 | 5/2013 | Mertens et al. | |
| 2013/0158627 A1 | 6/2013 | Gozani et al. | |
| 2014/0206945 A1 * | 7/2014 | Liao | A61N 1/36096 607/45 |
| 2014/0207032 A1 * | 7/2014 | Dematio | A61H 19/00 601/46 |
| 2014/0350327 A1 | 11/2014 | Poon et al. | |
| 2015/0101788 A1 * | 4/2015 | Smith | A61F 7/007 165/201 |
| 2015/0182375 A1 * | 7/2015 | Binversie | A61F 7/007 601/18 |
| 2015/0320588 A1 | 11/2015 | Connor | |
| 2016/0005320 A1 * | 1/2016 | deCharms | A61B 8/0808 434/236 |
| 2016/0012689 A1 | 1/2016 | Evreinov et al. | |
| 2016/0051182 A1 | 2/2016 | Zabaleta Rekondo et al. | |
| 2016/0147959 A1 * | 5/2016 | Mariottini | G16H 50/20 706/46 |
| 2016/0175140 A1 | 6/2016 | Chen et al. | |
| 2016/0246944 A1 * | 8/2016 | Jain | A61N 7/02 |
| 2016/0262924 A1 * | 9/2016 | Abreu | A41D 19/0027 |
| 2017/0056238 A1 * | 3/2017 | Yi | A61F 7/007 |
| 2017/0181915 A1 | 6/2017 | Ang et al. | |
| 2018/0042761 A1 | 2/2018 | Smith et al. | |
| 2018/0085055 A1 * | 3/2018 | Annoni | A61B 5/7275 |
| 2018/0110266 A1 * | 4/2018 | Lee | F25D 31/005 |
| 2019/0117444 A1 | 4/2019 | Smith et al. | |
| 2021/0085559 A1 | 3/2021 | Smith et al. | |

FOREIGN PATENT DOCUMENTS

| | | |
|---|---|---|
| CN | 101069769 A | 11/2007 |
| CN | 101300045 A | 11/2008 |
| CN | 102227694 A | 10/2011 |
| CN | 102974018 A | 3/2013 |
| CN | 104224312 A | 12/2014 |
| CN | 105147281 A | 12/2015 |
| CN | 106061456 A | 10/2016 |
| CN | 106618528 A | 5/2017 |
| CN | 106714899 A | 5/2017 |
| CN | 107205641 A | 9/2017 |
| JP | 2016-538972 A | 12/2016 |
| WO | WO 2016/149117 A1 | 9/2016 |
| WO | 2019/043482 A1 | 3/2019 |
| WO | 2019/046605 A1 | 3/2019 |
| WO | WO-2019043482 A1 * | 3/2019 ............ H01L 35/32 |

OTHER PUBLICATIONS

International Search Report and Written Opinion for International Application. No. PCT/US2018/050638, dated Dec. 7, 2018.
U.S. Appl. No. 17/109,790, filed Dec. 2, 2020, Smith et al.
U.S. Appl. No. 14/552,002, filed Nov. 24, 2014, Smith et al.
U.S. Appl. No. 16/214,372, filed Dec. 10, 2018, Smith et al.
U.S. Appl. No. 15/555,677, filed Sep. 5, 2017, Smith et al.
U.S. Appl. No. 29/574,277, filed Aug. 12, 2016, Shames et al.
PCT/US2018/050638, Dec. 7, 2018, International Search Report and Written Opinion.
Hussain et al., Ultrastretchable and flexible copper interconnect-based smart patch for adaptive thermotherapy. Adv Healthc Mater. Apr. 2, 2015;4(5):665-73. doi:10.1002/adhm.201400647. Epub Dec. 3, 2014.

* cited by examiner

HAPTIC ACTUATORS AND THEIR METHODS OF USE

RELATED APPLICATIONS

This application claims the benefit of priority under 35 U.S.C. § 119(e) of U.S. provisional application Ser. No. 62/571,311, filed Oct. 12, 2017, the disclosure of which is incorporated by reference in its entirety.

FIELD

Disclosed embodiments are related to haptic actuators and their methods of use.

BACKGROUND

Haptic actuators can be used to provide a variety of different thermal and/or physical sensations to a user to provide symptom relief for different types of conditions a user may have. For example, thermal dysregulation may be experienced by women that experience hot flashes, individuals with certain types of stroke or other traumatic brain injuries, and some individuals undergoing certain cancer treatments. To help alleviate the symptoms associated with thermal dysregulation, a haptic actuator may be used to provide a cooling sensation to the user. Similarly, a person that is prone to anxiety or panic attacks may be provided with physical sensations that are calming to the individual. For certain types of conditions, a medical practitioner may instruct a patient to maintain a log of episodes, and/or symptom severity, associated with the condition that the patient experiences since monitoring the symptoms of a condition may aid in successfully managing the experienced symptoms. For instance, when a patient recognizes that they have experienced a hot flash, a panic attack, or other type of episode associated with a condition, the patient may make note of the event as well as its severity in a diary that they subsequently provide to the medical practitioner for evaluation purposes. Alternatively, in cases where a particular condition does not have discrete episodes, a patient may simply keep a diary regarding the severity of symptoms throughout a day. In either case, this record may help provide a medical professional with a better understanding of the severity of a particular condition as well as its progression over time. This information may help a medical practitioner to make informed medical decisions with regards to how to treat the condition, as well as helping the patient to make more informed lifestyle decisions which may also help to reduce the severity of the experienced symptoms.

SUMMARY

In one embodiment, a method of operating a haptic actuator includes: detecting one or more states of a user; comparing the one or more states of the user to one or more predetermined activation parameters to determine if the user is experiencing an episode needing symptom relief associated with a condition of the user; and activating a haptic actuator to provide thermal and/or physical sensations to the user to provide subjective symptom relief, as perceived by the user, during the episode.

In another embodiment, a method of operating a haptic actuator includes: activating a haptic actuator to provide thermal and/or physical sensations to a user to provide subjective symptom relief, as perceived by the user, for a condition of the user; determining if the haptic actuator provided a desired amount of subjective symptom relief to the user; and updating one or more operating parameters of the haptic actuator if the haptic actuator did not provide the desired amount of subjective symptom relief to the user.

In yet another embodiment, a method of operating a haptic actuator includes: activating a haptic actuator to provide thermal and/or physical sensations to a user to provide subjective symptom relief as perceived by the user for a condition of the user; and recording information related to activation of the haptic actuator to create an event log associated with the condition, wherein the information includes at least one selected from the group of a timestamp, one or more operating parameters of the haptic actuator, and one or more states of the user.

In still another embodiment, a haptic actuator includes one or more thermal and/or physical actuators configured to apply thermal and/or physical stimulation to a user, and a controller operatively coupled to the one or more thermal and/or physical actuators. The controller is configured to: detect one or more states of a user; compare the one or more states of the user to one or more predetermined activation parameters to determine if the user is experiencing an episode needing symptom relief associated with a condition of the user; and activate the one or more thermal and/or physical actuators to provide thermal and/or physical sensations to the user to provide subjective symptom relief, as perceived by the user, during the episode.

In another embodiment, a haptic actuator includes one or more thermal and/or physical actuators configured to apply thermal and/or physical stimulation to a user, and a controller operatively coupled to the one or more thermal and/or physical actuators. The controller is configured to: activate the one or more thermal and/or physical actuators to provide thermal and/or physical sensations to a user to provide subjective symptom relief, as perceived by the user, for a condition of the user; determine if the haptic actuator provided a desired amount of subjective symptom relief to the user; and update one or more operating parameters of the haptic actuator if the haptic actuator did not provide the desired amount of subjective symptom relief to the user.

In yet another embodiment, a haptic actuator includes one or more thermal and/or physical actuators configured to apply thermal and/or physical stimulation to a user, and a controller operatively coupled to the one or more thermal and/or physical actuators. The controller is configured to: activate the one or more thermal and/or physical actuators to provide thermal and/or physical sensations to a user to provide subjective symptom relief as perceived by the user for a condition of the user; and record information related to activation of the haptic actuator to create an event log associated with the condition, wherein the information includes at least one selected from the group of a timestamp, one or more operating parameters of the haptic actuator, and one or more states of the user.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
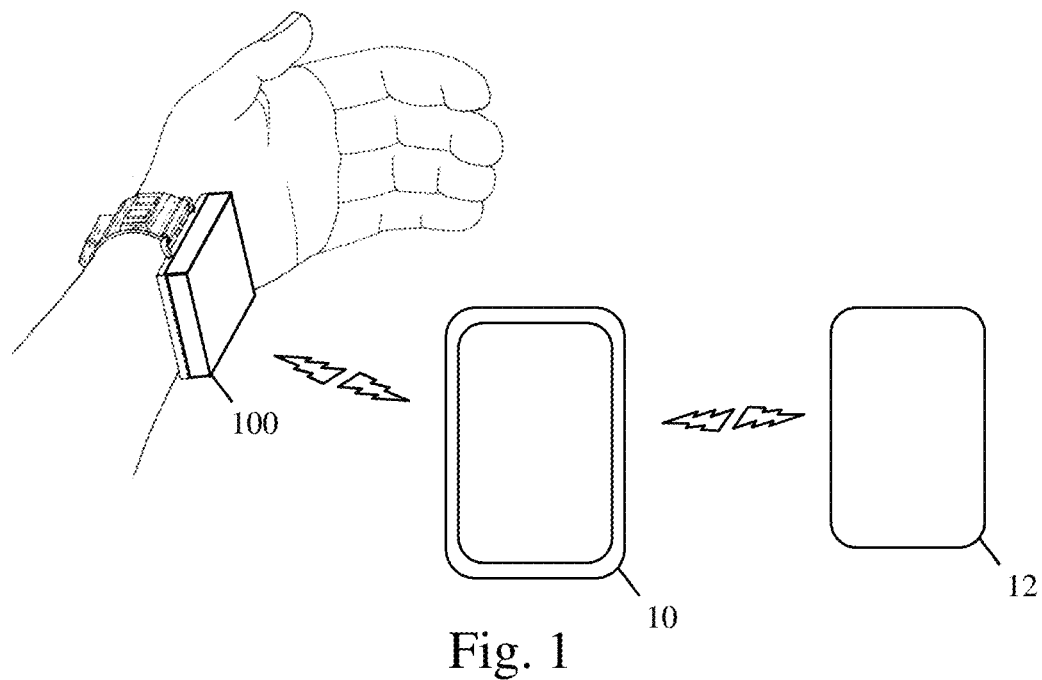
FIG. 1 depicts one embodiment of a haptic actuator located on a user's wrist that communicates with a separate computing device and/or a remotely located database.

Maintaining an accurate log of symptoms associated with one or more conditions of a patient offers several benefits. For example, an accurate log of symptoms may help enable a medical professional to make informed decisions regarding appropriate types of treatments and therapies and/or to make adjustments to those treatments and therapies based on their efficacy as shown in the symptom log. An accurate log of symptoms may also help a patient to better understand how their lifestyle decisions may be correlated with the degree and severity of symptoms they experience, thus, enabling them to make more informed behavioral decisions to effectively manage their symptoms. However, relying on self-reporting in symptom logs suffers from several deficiencies. Specifically, these logs rely on an individual to both accurately recognize the occurrence of episodes and/or objectively evaluate the severity of their symptoms over time. The patient must also then remember to record those events in the symptom log. This leads to a loss in both the accuracy and completeness of self-reported symptom logs.

In view of the above, the Inventors have recognized that it may be desirable to both provide improved symptom relief for patients suffering from a variety of conditions as well as improving the quality and accuracy of symptom logs for evaluation by patients and/or their associated medical professionals. Specifically, the Inventors appreciate that haptic actuators may be used to apply at least one of thermal and/or physical sensations to a user to provide a desired subjective sensation to the user for symptom relief for a variety of different types of conditions. However, due to physical and thermal sensations being extraordinarily subjective to individual users, the Inventors have recognized that patients may desire to personalize the physical and/or thermal sensations they experience, i.e. create individual settings for each user, to provide a desired subjective sensation for symptom relief for that individual user. Accordingly, the Inventors have appreciated that haptic actuators may be operated in ways that provide personalized symptom relief for patients. Further, the activation and personalization of these haptic actuators for individual users may be used to provide both an accurate log of when a haptic actuator is activated, which may be correlated with the occurrence of episodes of a condition and/or how often a user is requesting symptom relief for a particular condition, as well as providing previously unavailable information related to the type of symptom relief that a user requested as detailed further below. This information may be recorded over time to create a more objective and accurate log of the frequency and/or severity of symptoms experienced by a user over time as detailed further below.

In one embodiment, a haptic actuator may be activated either manually, or automatically, to provide at least one of thermal and/or physical sensations to a user to provide a desired subjective sensation to the user for symptom relief from a condition that the user suffers from. Activation of the haptic actuator, whether manual or automatic, may be considered an event associated with the condition. Accordingly, information related to the activation of the haptic actuator may be recorded to create a log of that activation event of the haptic actuator. While the recorded information may correspond to any appropriate type of information, in one embodiment, the information includes at least one of a timestamp when the actuator was activated, one or more operating parameters of the haptic actuator, and one or more sensed states of the user as well as combinations of the foregoing.

As noted above, in some embodiments, a controller of a haptic actuator may automatically activate the haptic actuator in response to the controller determining a user is experiencing a specific episode and/or symptoms with a perceived severity from the condition such that the user may desire symptom relief. However, due to the large variability between people, it is possible the controller may misidentify a situation where the user desires symptom relief. Accordingly, in some embodiments, after automatic activation of a haptic actuator, a controller of the haptic actuator may request that a user confirm that the user was experiencing an episode and/or symptoms where they wanted relief for. If the user indicates that activation of the haptic actuator was not desired, the controller may not record the event in the event log. This confirmation may occur either prior to, during, or after operation of the haptic actuator to help increase an accuracy of an event log. Of course, embodiment in which the accuracy of particular events are not confirmed prior to recordation are also contemplated as the disclosure is not so limited.

As noted above, the information obtained to form an event log related to a condition of a user when a haptic actuator is activated may correspond to any appropriate type of information that is of relevance to a medical practitioner and/or a user. For example, in addition to simply taking a timestamp (e.g. date and time) associated with identified events, the various user interactions associated with controlling and/or personalizing a haptic actuator to provide a desired subjective degree of symptom relief may also provide useful data that may be used to quantify a degree or severity of symptoms experienced by the user. Accordingly, one type of information that may be recorded includes a time of actuation which may provide insight into the time(s) of day episodes and/or symptoms are experienced and/or a frequency with which occur. Another type of information that may be recorded includes one or more operating parameters of a haptic actuator such as a duration of actuation and/or a degree of actuation. For instance, changes in the frequency of use and/or in the one or more operating parameters for actuation of a haptic actuator may be associated with changes in the degree of severity of symptoms experienced by a user. For example, increasing frequencies of use, durations, and/or intensities of actuation may be associated with more severe symptoms while decreasing frequencies of use, durations, and/or intensities of actuation may be associated with less severe symptoms. As detailed further below, in some embodiments, a haptic actuator may also include one or more sensors that sense information related to one or more states of a user and/or the surrounding environment. These sensed states of a user and environment may also be included in a log of events generated when a haptic actuator is activated to provide symptom relief for the user.

While several types of information are noted herein for use in creating a log associated with the activation events of a haptic actuator, it should be understood that the current disclosure is not limited to only the types of information described herein. Instead, any appropriate information related to a particular condition that is of interest to a user and/or a medical practitioner may be recorded during operation of a haptic actuator to create a log of events experienced by a particular individual using the haptic actuator.

As detailed further below, information recorded for events experienced by a user may either be recorded in local memory of a haptic actuator and/or an associated computing device, and/or the information may be transmitted to, and stored in, a remotely located database that is accessible to a patient and/or a medical practitioner. For example, information related to the various events may be stored on local memory of a haptic actuator and then separately transmitted to an associated computing device such as a smart phone, tablet, or computer. The information stored on the computing device may then be transmitted to the remotely located database. Alternatively, information may simply be transmitted directly to the database during the initial sensing and recordation process. In either case, an accurate and objective log related to the occurrence of events associated with the haptic actuator being activated to provide symptom relief to a user may be accurately and easily obtained.

The above noted event logs may be presented to users and/or their associated medical professions to help monitor symptom severity and frequency over time. This quantitative record of event information may be used to track changes in the severity and/or frequency of symptoms which may be correlated with a severity of the underlying condition. Thus, the user or a medical professional can use this log as an additional record for charting the evolution of the underlying condition, monitoring the effectiveness of treatments and/or therapies provided to a user, and/or correlating the experienced events with triggers present in a users' everyday life. Therefore, the currently disclosed systems and methods may be used to provide a more objective and accurate event log associated with events experienced by a user with a particular condition which may permit the user and their associated medical professionals to better monitor and treat a condition of the user over time.

In another embodiment, it may be desirable to provide a haptic actuator that is automatically actuated to apply at least one of thermal and/or physical sensations to provide symptom relief for a user when the user is experiencing symptoms from a condition of the user. For example, a controller of a haptic actuator may be operatively coupled to one or more sensors that sense one or more states of the user. The sensed one or more states may be compared to one or more predetermined activation parameters that are indicative of a user experiencing an episode with symptoms the haptic actuator may be used to at least partially alleviate. When the one or more states match the one or more predetermined activation parameters, indicating that the user is likely experiencing an episode with symptoms, a controller of the haptic actuator may automatically activate the haptic actuator to provide at least one of thermal and/or physical sensations to the user to provide symptom relief for the event.

Certain conditions exhibit symptoms that exist on a spectrum of severity, i.e. symptoms are not just experienced during discrete times. Instead, symptoms may be subjectively experienced with varying severity over time. This in contrast to symptoms that are only experienced during discrete times, such as experiencing thermal dysregulation during a hot flash. Accordingly, as used herein, an episode of a condition where a user may desire symptom relief may refer to both discrete episodes associated with symptoms that are only present during the time of that episode as well as episodes corresponding to a combination of factors where the user may desire symptom relief based on the subjectively perceived severity of the symptoms at that time even though the symptoms may be present at other times as well. For example, an episode may correspond to instances where a user desires symptom relief from the perceived severity of chronic pain, depression, anxiety, hypertension, insomnia, and/or other conditions that exhibit symptoms over a spectrum. Accordingly, it should be understood that an episode should not be limited to only conditions that exhibit symptoms during discrete times.

Due to the large variability in user states that different subjects exhibit when experiencing episodes with symptoms, it may be difficult to accurately identify when a user is experiencing an episode for automatically creating a record associated with that episode and/or automatically activating a haptic actuator to provide symptom relief. Accordingly, in some embodiments, it may be desirable to personalize the one or more predetermined activation parameters associated with a particular user to accurately identify when an episode needing symptom relief is occurring. In one such embodiment, a user may confirm whether or not an episode for which they desired symptom relief occurred after a haptic actuator is automatically activated based on a comparison of sensed states of the user to predetermined activation parameters stored within the local memory of the haptic actuator. The controller of the haptic actuator may also at least temporarily record one or more sensed states of a user when the haptic actuator is manually activated by a user to provide symptom relief during a self-identified episode. Due to the inclusion of user input in the form of episode confirmation and/or manual activation, the one or more sensed states of the user may then be identified as corresponding to an episode needing symptom relief or not for that particular user. Those one or more sensed states, including their classification as an episode or non-episode, may then be used to update the one or more predetermined activation parameters to improve the accuracy of episode identification by a controller of the haptic actuator for that user.

Updating of the one or more predetermined activation parameters associated with a particular user may be done in any appropriate way. For example, in one embodiment, when sensed states of a user resulted in the incorrect identification of an episode where a user desired symptom relief, the sensed states of the user may be used to negatively reinforce activation of the haptic actuator in response to that combination of sensed states. Correspondingly, when a user confirms that a controller of a haptic actuator accurately identified an episode during which they desired symptom relief, and/or when the user manually activates the haptic actuator to provide relief during a self-identified episode, the corresponding one or more sensed states of the user during these confirmed events may be used to positively reinforce activation of the haptic actuator in response to that combination of sensed states. Thus, the accuracy of a haptic actuator to identify episodes needing symptom relief for a particular user may be improved by the user actively using the actuator to provide the desired symptom relief and/or confirming the accuracy of automatically identified episodes needing symptom relief.

While the above embodiment describes the use of reinforcement learning to identify combinations of states of a user associated with a particular event, other appropriate types of learning algorithms may be used as the disclosure is not so limited. Alternative embodiments could use supervised, unsupervised, or reinforcement learning algorithms, including but not limited to Linear Regression, Naive Bayes, K-Nearest Neighbor (KNN), Decision Tree, Support Vector Machines (SVM), K-means Clustering (K-Means), Association Rules, Q-Learning, Temporal Difference, Deep Adversarial Networks, and/or any other appropriate algorithm capable of appropriately updating the activation parameters to control a haptic actuator using the sensed user states as described herein.

Depending on the particular embodiment, a haptic actuator may have an initial setting for the one or more predetermined activation parameters used to identify the occurrence of an episode needing symptom relief and/or for the operating parameters used to provide a desired sensation to the user for symptom relief. For example, a sternal skin conductance corresponding to a majority of individuals experiencing a hot flash may serve as an initial setting for the one or more predetermined activation parameters for people that experience hot flashes. These initial settings of the one or more predetermined activation parameters may then either be positively or negatively reinforced based on actual of episode data for an individual user as noted above. Alternatively, in another embodiment, the controller of a haptic actuator may initially record one or more sensed states of a user during any appropriate number of initial manually actuated activation events which may be assumed to correspond to self-identified episodes. These self-identified episodes as well as manually controlled operating parameters of the haptic actuator during those episodes may then form the basis of an initial data set used to identify one or more predetermined activation parameters and/or operating parameters associated for that user to identify episodes associated with a condition of that user for which they desire symptom relief, as well as to determine the operating parameters for providing a desired level of subjective symptom relief to that user. Appropriate forms of data analysis a controller, or coupled computing device, may use to determine the predetermined operating parameters include, but are not limited to, Linear Regression, Naive Bayes, K-Nearest Neighbor (KNN), Decision Tree, Support Vector Machines (SVM), K-means Clustering (K-Means), Association Rules, Q-Learning, Temporal Difference, Deep Adversarial Networks, or any other appropriate type of analysis algorithm. However, it should be understood that the other methods of setting an initial settings of a haptic actuator used to identify the occurrence of events needing symptom relief may be determined in any other appropriate manner as well.

The one or more sensed states of a user may be compared to the corresponding one or more predetermined activation parameters to identify the occurrence of an episode associated with a condition of the user in any appropriate fashion. For example, in some embodiments, the one or more states and predetermined activation parameters may be compared using detection thresholds, relative increases or decreases in signal strength related to the sensed state, durations of sensed states, the evolution of the sensed states over time, combinations of the foregoing, and/or any other appropriate method to enable the identification of these targeted episodes. For example, the occurrence of a hot flash for a user might be determined by detecting a sternal skin conductance that is greater than a lower threshold skin conductance for longer than a threshold amount of time.

It should be understood that depending on the particular condition a user has, the types of sensed states and predetermined activation parameters, as well as the values of these states and parameters, used to identify an episode of a user needing symptom relief will vary. Further, a sensed state of a user may correspond to a physiological state of the user and/or an affective state (e.g. psychological/emotional state) of a user. For example, non-limiting examples of states of a user that may be monitored include, but are not limited to: skin temperature; skin conductance/electrodermal activity; heart rate; heart rate variability/irregularity; blood pressure; brain/neuronal activity; respiratory rate; generalized physical activity levels; sleeping behavior and patterns; oxygen saturation levels; electrical activity of various muscles; observable behaviors of a user such as voice patterns, facial expressions, as well as body language and/or posture (e.g. tones and inflections of speech, facial expressions, and body language/posture may be associated with a user experiencing certain emotions and/or pain); environmental conditions the user is exposed to (e.g. temperature and humidity), self-reported physiological and/or affective state of a user (e.g. a user indicating a severity of an experienced symptom and/or emotional state of the user which may be input to a controller of a haptic actuator using any appropriate interface), combinations of the forgoing, and/or any other appropriate state of a user that may be correlated with a particular condition. Appropriate sensors that may be used to sense the states of a user, including those noted above, may include, but are not limited to: temperature sensors (e.g. thermocouples and thermistors) to measure skin temperature and/or environmental temperature; galvanic skin response sensors (e.g. electrodes placed on the skin) that measure electrodermal conductivity which may be indicative of various stress levels; accelerometers for measuring breathing rate, physical activity levels, sleeping behavior and patterns, etc.; optical physiological sensors, which in some embodiments may use optical spectroscopy, may be used to sense states such as temperature, heart rate/irregularities, and blood oxygen saturation levels; Holter monitors; electrocardiograms (ECG), chest strap sensors to measure heart rate and/or respiratory rates; electromyography (EMG) to sense electrical activity of muscles; voice recognition modules which may include one or more speakers (e.g. voice recognition analysis has been recognized as being able to evaluate certain emotional states of an individual including depression as well as whether or not an individual is in pain); facial recognition and body posture recognition modules which may include cameras or other optical detectors (facial expressions and body posture/language may be correlated with a user experiencing certain emotional states as well as whether or not the individual is feeling pain); combinations of foregoing, and/or any other appropriate sensor capable of detecting a desired state of a user.

The Inventors have recognized that the ability of a haptic actuator to provide symptom relief for a particular person depends entirely on how the applied stimuli is perceived by that individual. Further, how people perceive senses of touch, especially as it relates to thermal sensations, varies widely from person to person. A person's state and/or conditions they are afflicted with may also influence their somatosensory system which may change how that particular individual perceives sensations over time. Accordingly, giving a user the ability to customize one or more operating parameters of a haptic actuator to personalize the subjective relief they experience for a particular condition may provide both enhanced symptom relief and a new form of insight into the symptoms the user experiences that may be quantitatively monitored over time.

In view of the above, the Inventors have recognized the benefits associated with permitting a user to update one or more operating parameters of a haptic actuator either during, before, and/or after it has been used to provide symptom relief associated with a particular episode for a condition of the user. For example, a haptic actuator may be activated in response to any appropriate input, manual or automatic, to provide at least one of thermal and/or physical sensations to a user to provide symptom relief for a condition of the user. A controller of the haptic actuator may then determine if the haptic actuator provided a desired amount of symptom relief to the user based on the subjective perceptions of that individual user. This may be done in any number of ways including, for example, a verbal, audible, textual, graphical, or other appropriate prompt, provided to a user by the haptic actuator itself, or an associated computing device such as a smartphone or tablet implementing a graphical user interface, or other appropriate type of interface. The user may then indicate to the controller of the haptic actuator whether or not a desired amount of symptom relief was provided using any appropriate type of input device including, but not limited to, a touch screen, a keyboard, buttons, a motion recognition sensor such as an inertial measurement unit (IMU), a voice recognition system, an imaging system for gesture or facial expression recognition, and/or any other appropriate type of input device. In instances where a user indicates that the haptic actuator did not provide a desired amount of symptom relief, the user may be permitted to update one or more operating parameters of the haptic actuator as detailed below.

While the embodiment described above is directed to instances where operating parameters of a haptic actuator are updated after receiving input from a user that the subjective perception of the provided sensations did not provide a desired sensation, the current disclosure is not limited to only updating the parameters after receiving this type of input. For example, in another embodiment, a user may update operating parameters of a haptic actuator at any point during use including prior to, during, and/or after activation and operation of a haptic actuator to provide symptom relief without receiving prompting.

When it is desired to update the one or more operating parameters of a haptic actuator, these parameters may be updated using any appropriate method as the disclosure is not so limited. For example, in one embodiment, a user may simply manually adjust one or more of the operating parameters of a particular haptic actuator using any appropriate input device. Alternatively, a controller, or associated computing device, of a haptic actuator may simply prompt a user to indicate whether the user desires more aggressive or less aggressive symptom relief. The one or more operating parameters of the haptic actuator may then be updated using predetermined sets of operating parameters associated with varying amounts of symptom relief for a particular type of condition. For example, a request for more aggressive symptom relief may correspond to providing increased physical and/or thermal stimulation to a user, and a request for a less aggressive symptom relief may correspond to providing a decreased level of physical and/or thermal stimulation to the user. In one specific example, a more aggressive waveform and/or increased degree of cooling may be provided after a user suffering from hot flashes, or other form of thermal dysregulation, indicates that they desire a more aggressive cooling sensation. In some embodiments, these predetermined sets of operating parameters may be preloaded on a local storage of the haptic actuator and/or an associated computing device. Alternatively, in another embodiment, the predetermined sets of operating parameters associated with a particular condition may be pushed to the haptic actuator and/or an associated computing device from a remotely located computing device or database upon request for updated operating parameters.

As noted previously, in addition to permitting a user to update the operating parameters of a haptic actuator, in some instances, it may be desirable to record the one or more operating parameters of a haptic actuator that are applied during symptom relief to a user. This information may either be recorded locally on memory associated with a controller of the haptic actuator, on an associated computing device, and/or on a remotely located database. Over time, this may provide the user, and/or a medical practitioner overseeing treatment of the user, an objective log of events related to activation of the haptic actuator which may be correlated with episodes of a user's condition where a user desired symptom relief. The information included in this event log may include information related to the occurrence and/or severity of symptoms experienced by the user. For example, while particular indicators of a severity of symptoms experienced by a user may change depending on the specific condition that a user suffers from, generally lower magnitude temperatures and/or pressures, lower magnitude oscillations in the applied temperatures and/or pressures, shorter durations, less frequent actuation (on a, hourly, daily, weekly, or monthly time scale), and/or less aggressive waveforms may indicate less severe symptoms. Correspondingly, larger magnitude temperature and/or pressures, larger magnitude changes in temperature and/or pressures, longer durations, more frequent actuation (on a, hourly, daily, weekly, or monthly time scale), and more aggressive waveforms may indicate more severe symptoms. In either case, changes to the requested operating parameters over time may be correlated with various stimuli that a user may be exposed to as well as helping to objectively evaluate changes in experienced symptoms to evaluate the effectiveness of various treatments and/or therapies provided to the user. For example, if the requested symptom relief from a haptic actuator decreases in frequency and/or intensity, it may indicate an improvement in the underlying condition and/or that a particular treatment or therapy is effective in controlling the underlying condition.

As elaborated on below, a haptic actuator may be controlled using any appropriate type of operating parameter to provide a desired type of symptom relief using physical and/or thermal stimulation. For example, appropriate types of operating parameters may include, but are not limited to, waveform shape, rates of change, pulse intensity (i.e. delta between maximum and minimum applied stimuli), power profile, duration of operation, rest durations between physical pulses, frequencies, types of physical motion applied to a user, combinations of the forgoing, and/or any other appropriate type of operating parameter to tailor the applied physical and/or thermal sensations to provide a desired subjective sensation to a user.

In general, warm sensations and slow rhythms have been found to relax individuals due to their association with the perception of social touch by an individual. Similarly, cooling sensations have been found to provide a calming effect to individuals in a heightened emotional state. Also, faster pace rhythms may provide an energizing effect to a person experiencing them. For example, ranges of temperature that may be associated with energizing or relaxing warmth may be between 35-45° C. Ranges of temperature that may be associated with energizing or relaxing sensations of cool may be between 15-30° C. Separately, the effect of rhythmic sensations on physiological state of a person depends on the pace of the rhythm relative to the pace of the referenced physiological process, which for example could be a heart rate or respiratory rate in some embodiments. Therefore, what is perceived as relaxing or energizing may depend on the individual users' resting heart rate or respiratory rate. For respiratory rate, the average range for an adult may be between 12-18 breaths per minute (0.2-0.3 Hz), so example respiratory-like rhythms for relaxation may be between 10-15 breaths per minute (0.17-0.25 Hz). For heart rate, the average range for an adult may be between 50-100 beats per minute (0.8-1.7 Hz), and an example heartbeat-like rhythm for relaxation may be between 40-80 bpm (0.7-1.3 Hz). Conversely, an energizing rhythm may be between 0.25-0.33 Hz (energizing respiratory rate) or between 1.2-1.8 Hz (energizing heart rate). It should be understood that while particular temperatures and frequencies are provided above, embodiments in which different temperatures and/or frequencies both greater than and less than those noted above are used are also contemplated as the disclosure is not limited in this fashion.

Examples of applications for specifics types of stimulation for the control of symptoms associated with particular user conditions are provided below.

In one embodiment, a haptic actuator may provide cooling sensations to provide symptom relief to a user with a condition associated with experiencing thermal discomfort. Such conditions may include thermal discomfort associated with hot flashes from menopause; stroke or other traumatic brain injury; multiple sclerosis; various cancer treatments (e.g. prostate and breast cancer treatments may cause thermal dysregulation); or any other condition that may cause a person to experience thermal dysregulation. In embodiments where a haptic actuator is automatically activated, hot flashes for these users may be determined using a combination of parameters including a skin conductance, and in some embodiments, a sternal skin conductance, of the user that is greater than a predetermined skin conductance threshold.

In another embodiment, haptic actuators that provide either heating or cooling sensations may be used to provide emotional relief for managing symptoms associated with the experience of emotions that have strong thermal associations. For example depression, anxiety, insomnia, anger, loneliness, and sadness have strong correlations with experienced thermal sensations. Haptic actuators that apply physical sensations, such as a vibrotactile actuator, may also be used to provide emotional relief for symptoms associated with elevated states of arousal, where slow rhythms may be used to promote a parasympathetic response to calm an individual. As detailed in the embodiments below, haptic actuators that provide both thermal and physical sensations to provide symptom relief from heighted emotional states are also contemplated.

In one embodiment, a haptic actuator may provide cooling sensations and/or slow rhythmic physical stimulation to calm a user experiencing a panic attack. The occurrence of a panic attack for automatic activation of the haptic actuator may be determined using a spike in heart rate though other appropriate user states may be used instead or in combination to help identify a panic attack. For example, an increase in heart rate greater than a threshold heart rate increase for a given time period may be indicative of a panic attack.

In yet another embodiment, a haptic actuator may be used to provide symptom relief for depression, anxiety, hypertension, and/or insomnia of a user. In such an embodiment, the haptic actuator may provide warming thermal sensations, cooling thermal sensations, and/or slow rhythmic physical sensations to relax the user. An inertial measurement unit (IMU) may be used to monitor activity levels during sleep to monitoring symptoms of insomnia. Measurements of activity levels, speech intonations, or skin temperature may be used to monitor increases in symptoms of depression. Symptoms related to anxiety or hypertension may be related to indicators of physiological arousal, such as heart rate, heart rate variability, blood pressure, or skin conductance. Of course, it should be understood that the above noted user states may be used in combination to help improve reliable monitoring of a targeted symptom of a user.

In still another embodiment, a haptic actuator may provide symptom relief associated with chronic pain including, for example, chronic neck pain which is the most common form of chronic pain. In such an embodiment, a haptic actuator may provide warming thermal sensations and/or vibrations to the site of pain to provide symptom relief. The physical state of the user and detection of symptoms related to chronic pain may include the use of: electromyography (EMG) for detecting heightened local muscle contraction; one or more IMU for monitoring body positions or postures associated with pain; facial or voice recognition for identifying when chronic pain is being experienced; and/or any other appropriate user state. General measures of autonomic arousal may also provide physiological information related to the experience of chronic pain (e.g. heart rate, heart rate variability, skin conductance).

While certain combinations of user conditions and associated user states are described above, the disclosure is not limited to only those combinations of conditions and user states described herein. Thus, the user states noted above may be combined with, or replaced by, one or more other user states as disclosed herein to provide a more accurate identification of episodes where symptom relief may be desired. For example, combining one or more of the above noted user states with determinations of the emotional state of a user, environmental conditions such as temperature and humidity the user is exposed, and/or other appropriate user states may help provide a more complete understanding of how a user subjectively experiences symptoms of a particular condition. Further, this combination of factors may permit a more accurate determination of whether or not a particular individual desires symptom relief when exposed to that combination of states.

In some instances, a haptic actuator may be capable of being used for any number of different types of user conditions. In such an environment, the haptic actuator may include a number of standard sensors and/or inputs for determining different types of user states. In such an embodiment, the controller of the haptic actuator may detect all of the available user states and appropriate correlations between those detected user states and episodes during which a user may wish symptom relief may be determined using appropriate algorithms as described herein over time as the user continues to use the haptic actuator for symptom relief. For example, if a controller determines that certain user state inputs have little correlation with episodes of a particular condition, the predetermined activation parameters of a haptic actuator may be negatively reinforced to place little, or no emphasis, on those user states. Conversely, if the controller determines that particular user states exhibit a stronger correlation with episodes where a user wishes symptom relief, the controller may positively reinforce the use of those user states within the predetermined activation parameters of a haptic actuator. Thus, a controller of a generic haptic actuator that may be used to provide symptom relief for a number of different conditions may be reconfigured as it is used to recognize and activate the haptic actuator in response to user states associated with a particular condition.

In the above embodiment, appropriate forms of data analysis a controller, or coupled computing device, may use to determine these predetermined operating parameters include, but are not limited to, Linear Regression, Naive Bayes, K-Nearest Neighbor (KNN), Decision Tree, Support Vector Machines (SVM), K-means Clustering (K-Means), Association Rules, Q-Learning, Temporal Difference, Deep Adversarial Networks, or any other appropriate type of analysis algorithm.

As used herein, a haptic actuator may refer to a device that is configured to generate thermal and/or physical sensations that may be perceived by a user for the purpose of providing symptom relief for a condition of the user. Thermal and physical sensations may correspond to sensations perceived by a user through their sense of touch as it applies to sensing pressures and/or temperatures applied to the skin of a user. Appropriate types of haptic actuators include, but are not limited to: thermal actuators using a variety of thermal technologies including thermoelectric materials and resistive heating elements; vibrotactile actuators; pressure cuffs (e.g. bands including electroactive polymers and/or inflatable air bladders); mechanical stroking and/or caressing actuators such as variable stiffness and variable impedance actuators; and/or any other appropriate type of device capable of applying a desired physical and/or thermal stimulation to a user.

Sensations provided by a haptic actuator may either be applied at a static location on a user's body, and/or a haptic actuator may apply sensations that move relative to a portion of a user the haptic actuator is disposed on. For example, a sensation from a haptic actuator may be applied to a user using a component that may move in a linear reciprocating motion, a rotational motion, and/or in any other appropriate type of motion relative to a portion of a user's body. Specific examples of components that may be used to provide this desired type of motion include, but are not limited to, Eccentric Rotating Mass Motors, Linear Resonant Actuators, Piezoelectric Drivers, Solenoid Drivers, and/or Tactile Transducers.

One specific example of a haptic actuator that may be used to provide thermal stimulation to a user, as well as its method of operation, is described in International Patent Application No. PCT/US2014/060100 filed Oct. 10, 2014 and International Patent Application No. PCT/US2016/022105 filed on Mar. 11, 2016, the disclosures of each of which are incorporated herein by reference in their entirety.

As detailed above, haptic actuators may provide psychophysiological relief for a variety of different user conditions by leveraging the body's natural response to thermal and physical sensations as subjectively perceived by a user. The various operating parameters that may be associated with the control of a haptic actuator to provide a desired degree of symptom relief using thermal and/or physical stimulation may include, but are not limited to, magnitude of warming and/or cooling (i.e. magnitude change temperature); magnitude of applied pressure, frequency of temperature changes and/or pressure changes (slow rhythmic pressure versus high-frequency vibrations), rates of change in temperature and/or pressure, the change in temperature and/or pressure during individual cycles of an applied profile, shape of the applied wave form, and/or any other appropriate operating parameter as the disclosure is not so limited.

While several specific types of haptic actuators are described above, it should be understood, that a haptic actuator configured to provide symptom relief for a specific type of condition may provide any desired combination of physical and/or thermal stimulation to a user. Accordingly, a haptic actuator may provide only thermal stimulation, only physical stimulation, and/or a combination of thermal and physical stimulation to a user as the disclosure is not so limited.

In addition to the above, depending on the particular condition that a haptic actuator is intended to provide symptom relief for, the haptic actuator may be incorporated into any number of different wearable components that may be positioned adjacent to different portions of a user's body. For example, a haptic actuator may be incorporated into an article of clothing (e.g. scarf, necklace, shirt, dress, pants, shorts, gloves, socks, etc.), a band or sleeve that may be worn on a portion of the body (e.g. armbands, wristbands, bracelet, ankle bracelet, legging, compression sleeve, etc.), as well as any other garment or other configuration capable of retaining a haptic actuator adjacent to a desired portion of a user's body. Correspondingly, a haptic actuator may be positioned and maintained adjacent to any number of different portions of a user's body including, but not limited to, a user's arm, wrist, chest, neck, torso, waist, leg, ankle, and/or any other appropriate portion of a user's body as the disclosure is not so limited.

As noted previously, a user interface for displaying queries and/or other outputs to a user as well as receiving input from a user may be provided in any number of different ways. For example, a user interface including a display and/or user input device may be integrated with a haptic actuator and/or it may be included in a separate computing device that the haptic actuator is either in wired, or wireless communication with. Thus, a user interface may include a computer, a smartphone, a tablet, a touchpad, a keyboard, a display, a speaker, a microphone, an inertia measurement unit (IMU), combinations of the above, or other appropriate configurations. In one specific embodiment, an IMU may be used to monitor taps applied to the device and/or gestures of the user to provide inputs to a haptic actuator such as start actuation, end actuation, increase or decrease a desired parameter, indicate yes or no in response to a query, and/or any other appropriate types of input. For example, tapping the haptic actuator once may indicate yes to a query from the haptic actuator and tapping the haptic actuator twice may indicate no to the query, though other gestures may also be used for various types of inputs.

As used herein, when an element, component, layer, and/or surface are referred to as being "adjacent", it may be directly adjacent, or an intervening element, component, layer, and/or surface may also be present. A layer or component that is "directly adjacent" another element, component, layer, and/or surface means that no intervening element, component, layer, and/or surface is present.

A number of embodiments described herein refer to a wireless communicator used to provide communication between a haptic actuator and one or more of an associated computing device and/or a remotely located database. It should be understood that a wireless communicator may correspond to any appropriate device or component that enables a haptic actuator to communicate wirelessly including devices that communicate using RF, Bluetooth, Wi-Fi, or any other suitable wireless communication protocol. However, it should be understood that the currently disclosed haptic actuators and methods of operation are not limited to only being used with devices that include wireless communication. For example, a haptic actuator may simply be designed for standalone use without any external communication, or the haptic actuator may include one or more communication ports that may be used for periodic downloads to, and/or uploads from, a connected computing device or database.

Turning now to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 depicts one embodiment of a haptic actuator 100 that may be used to provide at least one of thermal and/or physical stimulation to a user to provide symptom relief for a condition of the user. In the depicted embodiment, the haptic actuator is in the form of a bracelet worn on the wrist of a user 102. However, as noted previously, the haptic actuator may be disposed adjacent to any appropriate portion of the user's body and may be integrated into any appropriate garment or other component that may maintain the haptic actuator in the desired location on the user's body. In some embodiments, the haptic actuator is in wireless communication with a separate computing device 10 which may function as a user interface, and in some instances, a controller of the haptic actuator. For example, a user may use a graphical user interface (GUI), buttons, keypad, or other appropriate interface provided on the computing device to activate the haptic actuator to provide symptom relief during an episode the user is experiencing, respond to prompts related to operation of the haptic actuator, and/or to adjust one more operating parameters of the haptic actuator.

As discussed above, in some embodiments, it may be desirable to record various types of information when a haptic actuator is used to provide symptom relief for an event related to a condition of a user. In such an embodiment, a haptic actuator 100 and/or a computing device 10 that the haptic actuator is in communication with may transmit and/or receive information from a remotely located database 12. For example, the remotely located database may be associated with a database maintained by a medical practitioner overseeing the therapy and treatment of a particular user using the haptic actuator. Accordingly, information related to the operation of the haptic actuator, for example, a timestamp, one or more operating parameters of the haptic actuator, one or more states of a user, combinations of the above, and/or any other appropriate type of information related to the operation of the haptic actuator during an event may be recorded on a local memory of the haptic actuator and/or computing device for subsequent transmission to the remotely located database. Alternatively, the information may simply be transmitted to the remotely located database without maintaining a separately recorded log of the event on a local memory as the disclosure is not so limited. Additionally, in some embodiments, the information may not be transmitted to a remotely located database and instead may simply be recorded on local memory of the haptic actuator and/or computing device.

Figure 2:
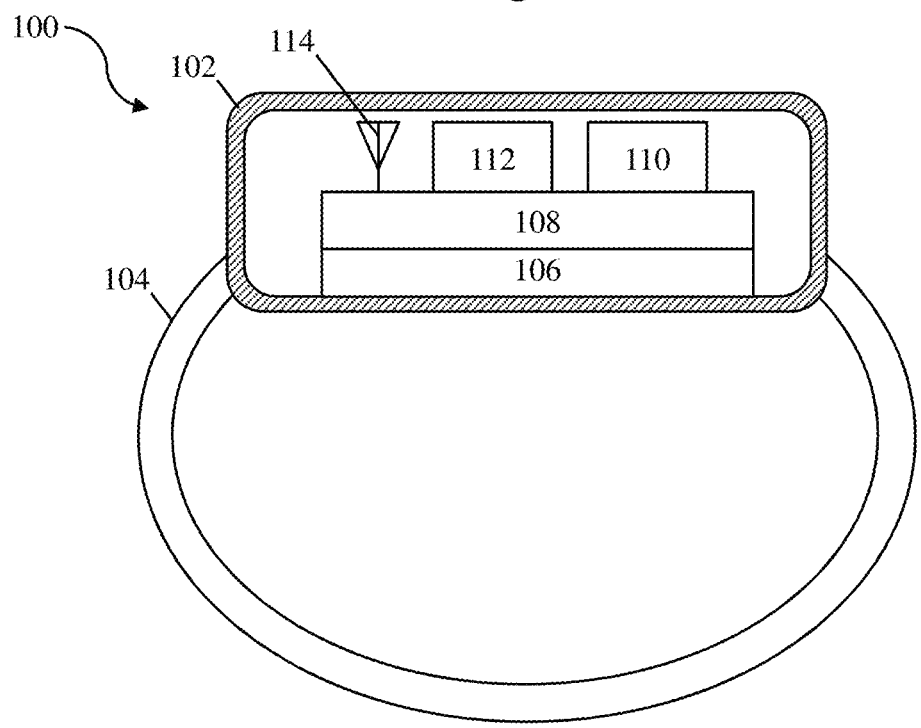
FIG. 2 depicts an embodiment of a haptic actuator including a wireless communicator as well as one or more sensors.

FIG. 2 depicts a schematic embodiment of a haptic actuator 100. In the depicted embodiment, the haptic actuator includes a housing 102 and a band 104 that is configured to maintain the haptic actuator adjacent to a desired portion of a user's body. Within the housing, the haptic actuator may include one or more thermal or physical actuators 106 that may be configured to apply thermal and/or physical stimulation to an associated part of a user's body that the haptic actuator is disposed adjacent to. The haptic actuator includes a controller 108 that is operatively coupled to the one or more thermal or physical actuators. The haptic actuator may also include one or more sensors 110 that are operatively coupled to the controller. The sensors are configured to sense one or more states of a user as previously discussed. While the one or more sensors have been depicted as being included inside the housing 100, in some embodiments, the one or more sensors may be located outside of the housing, and may even be located on different portions of a body for sensing a particular state of the user. The haptic actuator may also include a battery 112 and wireless communicator 114 that is are operatively coupled to the controller.

While the haptic actuator depicted in the above embodiment includes a band, it should be understood that the haptic actuator may be incorporated into any other appropriate type of wearable device, component, or garment as previously discussed.

Figure 3:
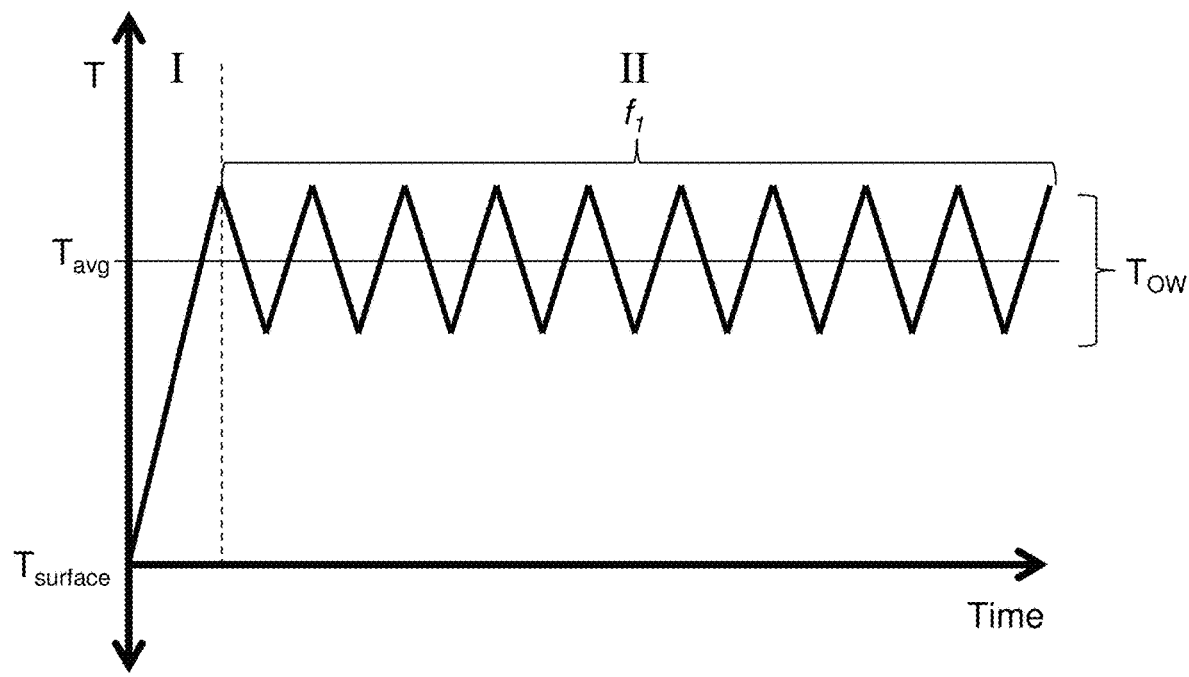
FIG. 3 is a graph of one embodiment of a series of thermal pulses that may be applied to a user by a haptic actuator.

To provide a desired type of symptom relief, a haptic actuator may provide different types of thermal stimulation. One specific embodiment of a thermal profile that may be applied to a corresponding portion of a user's body is depicted in FIG. 3. In the depicted graph, a temperature of the haptic actuator is illustrated relative to an initial temperature of a surface the haptic actuator is disposed against. For the sake of clarity, the depicted embodiment illustrates temperatures that are greater than a corresponding temperature of the surface the haptic actuator is disposed against (i.e. the haptic actuator provides a warming sensation). However, the current disclosure is not limited in this fashion. For example, the haptic actuator may be operated to apply temperatures that are less than a corresponding initial temperature of the surface to provide a cooling sensation to a user. Additionally, embodiments in which both heating and cooling sensations are alternatingly applied with temperatures both greater than and less than the initial temperature of the surface are also contemplated.

As shown schematically in the figure, a thermal profile may have one or more portions including a ramp profile portion and/or one or more alternating thermal profile portions, i.e. one or more thermal pulses. For example, the thermal profile may comprise a first portion comprising a ramp profile portion (regime I) and a second portion comprising an alternating thermal profile portion (regime II) where the temperature of the haptic actuator cyclically varies between at least a first higher temperature and a second lower temperature. In some embodiments, the alternating thermal profile portion may have an average frequency corresponding to the number of thermal pulses applied per unit time, $f_1$, an average temperature, $T_{avg}$, and an oscillation window, $T_{ow}$. The oscillation window is the difference between the maximum and minimum temperature for a given alternating thermal profile. The average temperature, $T_{avg}$, may be equal to a time average of the temperature, and thus may change depending on if the rates of increase and decrease of the temperature between the first higher temperature and the second lower temperature are different and/or if there are any constant temperature portions associated with the thermal pulses.

Figure 4:
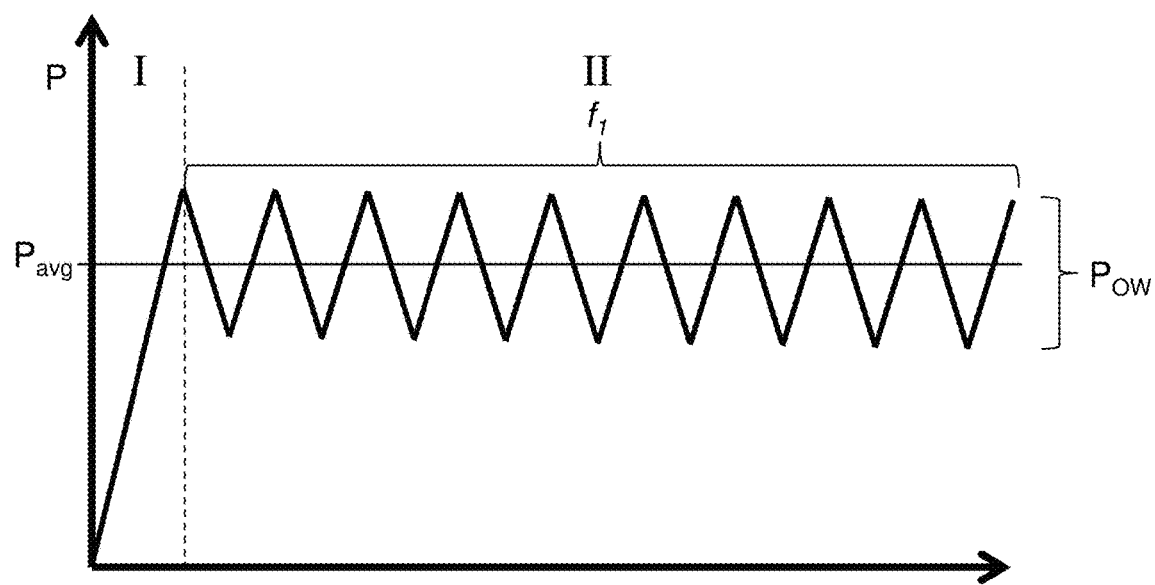
FIG. 4 is a graph of one embodiment of a series of pressure pulses that may be applied to a user by a haptic actuator.

Similar to the description of a thermal profile provided above, FIG. 4 schematically depicts one possible embodiment of a pressure profile applied to a corresponding portion of a user's body. The pressure profile may have one or more portions including a ramp profile portion and/or one or more alternating pressure profile portions, i.e. one or more pressure pulses. For example, the thermal profile may comprise a first portion comprising a ramp profile portion (regime I) and a second portion comprising an alternating pressure profile portion (regime II) where the pressure of the haptic actuator cyclically varies between at least a first higher pressure and a second lower pressure, which depending on the particular embodiment may be zero pressure (i.e. a rest period) or an intermediate pressure less than the first pressure. In some embodiments, the alternating pressure profile portion may have an average frequency corresponding to the number of pressure pulses applied per unit time, $f_1$, an average pressure, $P_{avg}$, and an oscillation window, $P_{ow}$. The oscillation window is the difference between the maximum and minimum pressure for a given alternating pressure profile. The average pressure, $P_{avg}$, may be equal to a time average of the pressure, and thus may change depending on if the rates of increase and decrease of the pressure between the first higher pressure and the second lower pressure are different and/or if there are any constant pressure portions associated with the pressure pulses.

While the above noted figures depict saw-tooth temperature and pressure profiles, it should be understood that these profiles are for illustrative purposes and that the actual profiles applied during operation of a haptic actuator may exhibit any desired type of waveform. For example, a particular thermal and/or pressure pulse may have profiles that exhibit substantially linear, non-linear, exponential (e.g., exponential growth, exponential decay), polynomial (quadratic, cubed, etc.), irregular (e.g., following a piecewise function), sinusoidal, or other suitable behaviors. A thermal or pressure profile may also include one or more constant temperature or pressure portions associated with the one or more pulses. In one such embodiment, a thermal or pressure pulse may include one or more portions where the temperature and or pressure is maintained at a value for a predetermined duration of time. This constant section of a pulse may be applied at a maximum, minimum, and/or an intermediate temperature or pressure of the pulse. In one such embodiment, a pressure profile may include a cyclic substantially stepwise change in pressure applied to a user between a first higher pressure and a second lower pressure. Additionally, while the rates of change in temperature and pressure during the cyclically applied pulses has been depicted in the figures as equal during the increasing and decreasing portions of the pulses, the current disclosure is not limited in this fashion. Specifically, the applied thermal and pressure pulses may exhibit different magnitudes in the rate of change during an increases in temperature or pressure and during decreases in temperature or pressure. For example, a thermal pulse may increase to a desired maximum temperature rapidly while it may cool back to a lower temperature at a relatively slower rate, or vice versa. Of course, while cyclic thermal and pressure pulses have been described above, it should be understood that in some embodiments it may be desirable for haptic actuator to simply apply and hold one or more temperatures or pressures for a predetermined time duration without cycling between temperatures or pressures as the disclosure is not limited to only applying cyclic sensations.

Based on the above, illustrative examples of operating parameters that may be used to control thermal and/or physical sensations applied to a user by a haptic actuator may include, but are not limited to: wave form shapes, rates of change, magnitudes/intensities of the applied pressures and temperatures; maximum and minimum applied temperatures or pressures (i.e. oscillation window); cycle frequency; duration of actuation; and combinations of the forgoing. In instances where a haptic actuator is capable of moving a location at which a thermal or physical sensation is applied relative to a portion of a user's body (e.g. movable pressure actuators and/or thermal actuators that rotate, move linearly, and/or otherwise may move relative to a user's body), the operating parameters of the haptic actuator may also include a pattern and/or frequency in which the thermal and/or pressure actuator may be moved relative to an associated portion of a user's body.

Figure 5:
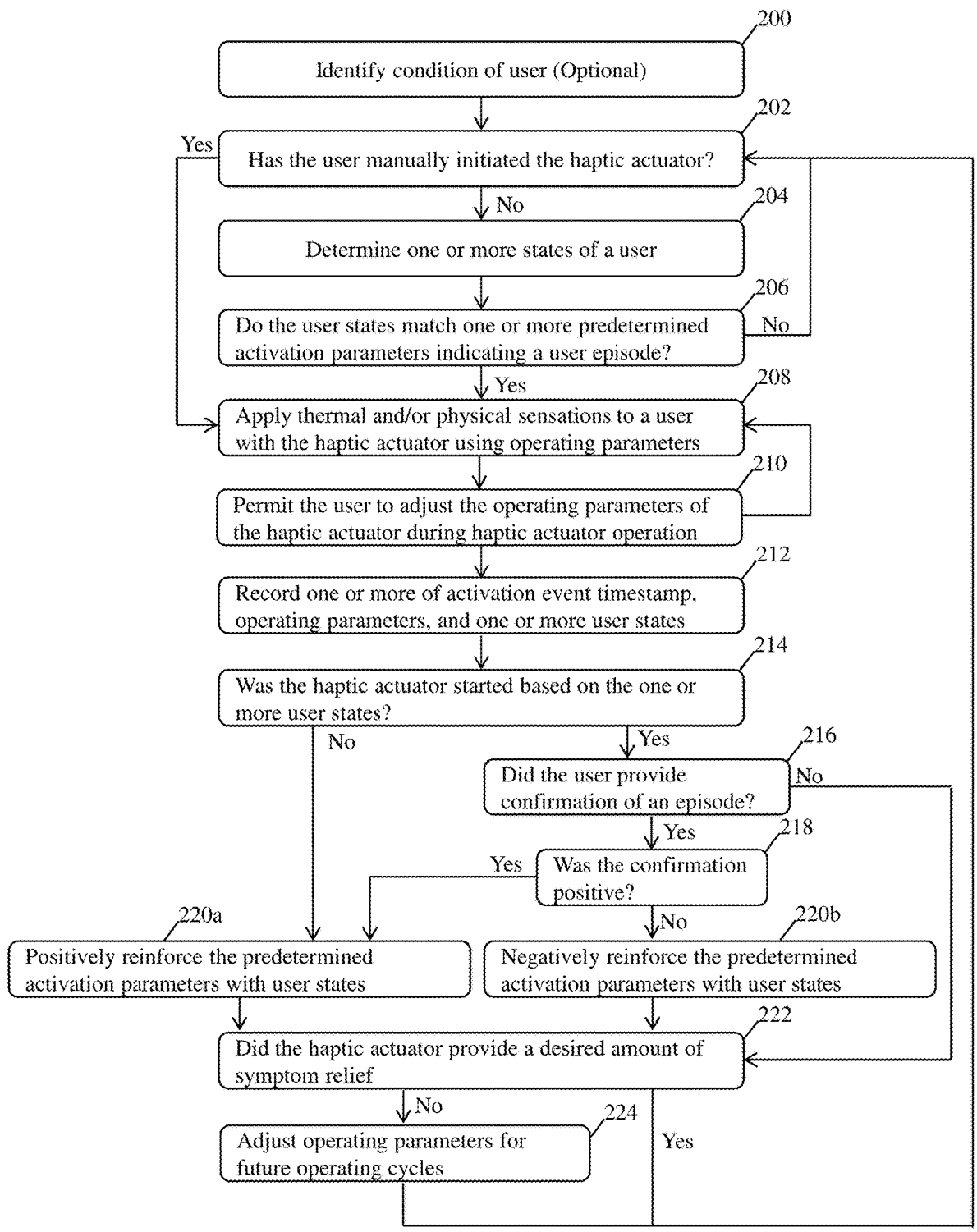
FIG. 5 is a flow diagram of a method for operating a haptic actuator to provide personalized symptom relief and automatic activation as well as record a log of the occurrence of events associated with a user's condition.

FIG. 5 depicts one embodiment of a method for operating a haptic actuator and recording information related to events determined based on the activation of the haptic actuator to provide symptom relief for a user. For the sake of clarity, the depicted method is described in relation to a controller of the haptic actuator. However, embodiments in which an associated computing device that the haptic actuator is in communication with may perform one or more of the steps described below are also contemplated.

When a user first receives a haptic actuator, a controller of the haptic actuator may identify a condition that the user has, and initialize the various operating parameters and predetermined activation parameters that may be used to identify episodes where the user may desire symptom relief, see 200. For example, a user may simply input, or select from a list presented in a GUI, which particular condition they have. These initial settings for the operating parameters and/or predetermined activation parameters for a haptic actuator may correspond to settings that have been determined to provide an adequate degree of symptom relief and accuracy in identifying episodes for a population of user's, or a standard group of subjects that have been evaluated under controlled situations, having the same condition. Alternatively, in some embodiments, a particular haptic actuator may already be configured for use with a particular condition, and therefore may not specifically identify the condition of a particular user prior to a first operation.

During normal operation, a controller of a haptic actuator may determine whether or not a user has manually initiated operation of the haptic actuator at 202. A user may manually initiate operation of a haptic actuator using any appropriate user interface including buttons, keypads, touchpads, gesture recognition, voice command, as well as through the use a paired computing device such as a smart phone or tablet, or any other appropriate interface. If the user has manually initiated operation of the actuator operation may continue to 208 where the haptic actuator applies a desired thermal and/or physical sensation to a user for symptom relief using the one or more operating parameters. If the user did not manually request operation of the haptic actuator, the controller may proceed to step 204 where one or more sensors associated with the controller determine one or more states of the user. Again these states of the user may be determined using one or more sensors as described previously, and/or a user may provide input regarding self-reported user states such as a self-reported physiological and/or affective state using an appropriate interface with the haptic actuator. For example, a user may indicate a severity of an experienced symptom and/or an emotional state of the user. Once the one or more user states are determined, the controller may then compare the one or more user states to one or more predetermined activation parameters using any of the previously mentioned comparison methods to determine if the user is experiencing an event associated with the identified condition where symptom relief may be desired, see 206. If the sensed states of a user are consistent with the user experiencing an episode associated with the condition where symptom relief may be desired, the controller may automatically start operation of the haptic actuator to apply thermal and/or physical sensations to the user to provide symptom relief at 208. However, if the sensed states of the user do not match the predetermined activation parameters, the controller may continue to monitor for manual activation of the haptic actuator as well as determining if the user is experiencing an episode associated with the identified condition of the user.

In some instances the thermal and/or physical sensations applied to a user when activated may not provide a subjective sensation, as perceived by the user, to provide a desired intensity of symptom relief. Accordingly, a controller of a haptic actuator may be configured to permit a user to update one or more operating parameters of a haptic actuator during operation to alter the applied sensations to provide a desired amount of symptom relief as perceived by that user at 210. Of course it should be understood that the user may alter the operating parameters both before and after an activation event of the haptic actuator as well as the disclosure is not so limited.

In some embodiments, prior to, during, or after operation of a haptic actuator to provide symptom relief to a user, i.e. after an event where the haptic actuator has been activated, one or more of a timestamp associated with the event, one or more operating parameters of the haptic actuator, one or more sensed states of the user, and/or a combination of the foregoing may be recorded to provide a log of events, see 212. Again, this information may be recorded in local memory associated with the haptic actuator, a computing device paired with the haptic actuator, and/or on a remotely located database.

To improve the accuracy of a controller of a haptic actuator in identifying episodes needing symptom relief associated with a particular condition of a user, in some embodiments, a controller may confirm whether or not an episode identified by the controller actually occurred. Specifically, in one embodiment, at 214, if the controller of the haptic actuator automatically initiated operation of the haptic actuator based on one or more detected states of the user, the controller may confirm whether or not an episode was accurately identified at 216. The controller may confirm this with the user using any appropriate form of inquiry and corresponding input from the user. If the user positively indicates that the controller accurately identified an episode associated with the condition of the user at 218, i.e. provides positive confirmation, or if a user manually initiated operation of the haptic actuator to provide symptom relief, which may also be taken as confirmation of an episode, the controller of the haptic actuator may positively reinforce one or more predetermined activation parameters used to identify events with the one or more determined states of the user during the episode, see 220a. In contrast, if the user indicates that the controller incorrectly identified an episode associated with the condition at 218, i.e. provided a negative confirmation, the controller of the haptic actuator may negatively reinforce the one or more predetermined activation parameters with the one or more determined states of the user when the event was incorrectly identified, see 220b. Alternatively, if the user does not confirm whether or not a controller correctly identified an episode needing symptom relief, controller may maintain the current set of predetermined activation parameters without any changes or reinforcement during that operation cycle. Accordingly, increased usage of the haptic actuator to provide symptom relief for a particular user may lead to a personalized, and thus more accurate, set of predetermined activation parameters used to determine whether or not that particular user is experiencing an episode where it may be desirable to activate a haptic actuator to provide symptom relief. While a reinforcement learning protocol has been described above, it should be understood that other appropriate protocols may be used to help improve the accuracy of event identification using the additional information provided by manual initiation and confirmation of episodes from a user.

As noted above, to help improve the application of an appropriate amount of symptom relief using a haptic actuator, in some embodiments it may be desirable to permit a user to personalize the operation of a haptic actuator to provide a desired degree of symptom relief. Accordingly, as indicated at 222, in some embodiments, a controller of a haptic actuator may request input from a user using any appropriate interface to indicate whether or not operation of the haptic actuator provided a desired amount of symptom relief during the last activation event, i.e. during the corresponding episode for which the user wanted symptom relief. If the user indicates that the haptic actuator provided a desired amount of symptom relief, the controller may simply maintain the current operating parameters of the haptic actuator and return to step 202 awaiting the next activation.

In contrast to the above, if a user indicates that a haptic actuator did not provide a desired amount of symptom relief at 222, the controller may proceed to step 224 where the one or more operating parameters of the haptic actuator may be adjusted for use during future operating cycles as detailed below. After updating the operating parameters of the haptic actuator, the controller may proceed back to step 202 to begin the process again.

Adjusting the operating parameters of a haptic actuator, whether done during or after operation of a haptic actuator to provide symptom relief, may be done in any appropriate fashion. For example in one, a user may simply manually adjust the one or more operating parameters of the haptic actuator using an appropriate interface. In another embodiment, a user may select between different predetermined sets of operating parameters to apply different intensities of thermal and/or pressure sensations to provide a desired subjective symptom relief for that individual user. In yet another embodiment, a user may simply indicate that they wish to have either an increased or decreased intensity of symptom relief provided by the haptic actuator. In such an embodiment, the controller of a haptic actuator may simply select a more or less aggressive thermal and/or pressure profile to provide the desired subjective amount of symptom relief. In both of these embodiments, these predetermined sets of operating parameters may either be stored locally on the controller of the haptic actuator and/or they may be pushed out to the controller from a remotely located computing device and/or database when a request is received from a controller of a haptic actuator requesting updated operating parameters to provide the requested amount of sensation to a user. Thus, a user may personalize the operation of a haptic actuator to provide a desired subjective amount of symptom relief as they continue to use the haptic actuator.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computing device or distributed among multiple computing devices. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computing device may be embodied in any of a number of forms, such as a rack-mounted computer, a desktop computer, a laptop computer, or a tablet computer. Additionally, a computing device may be embedded in a device not generally regarded as a computing device but with suitable processing capabilities, including a Personal Digital Assistant (PDA), a smart phone, tablet, or any other suitable portable or fixed electronic device.

Also, a computing device may have one or more input and output devices. These devices can be used, among other things, to present a user interface. Examples of output devices that can be used to provide a user interface include display screens for visual presentation of output and speakers or other sound generating devices for audible presentation of output. Examples of input devices that can be used for a user interface include keyboards, individual buttons, and pointing devices, such as mice, touch pads, and digitizing tablets. As another example, a computing device may receive input information through speech recognition or in other audible format.

Such computing devices may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the embodiments described herein may be embodied as a computer readable storage medium (or multiple computer readable media) (e.g., a computer memory, one or more floppy discs, compact discs (CD), optical discs, digital video disks (DVD), magnetic tapes, flash memories, RAM, ROM, EEPROM, circuit configurations in Field Programmable Gate Arrays or other semiconductor devices, or other tangible computer storage medium) encoded with one or more programs that, when executed on one or more computers or other processors, perform methods that implement the various embodiments discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computing devices or other processors to implement various aspects of the present disclosure as discussed above. As used herein, the term "computer-readable storage medium" encompasses only a non-transitory computer-readable medium that can be considered to be a manufacture (i.e., article of manufacture) or a machine. Alternatively or additionally, the disclosure may be embodied as a computer readable medium other than a computer-readable storage medium, such as a propagating signal.

The terms "program" or "software" are used herein in a generic sense to refer to any type of computer code or set of computer-executable instructions that can be employed to program a computing device or other processor to implement various aspects of the present disclosure as discussed above. Additionally, it should be appreciated that according to one aspect of this embodiment, one or more computer programs that when executed perform methods of the present disclosure need not reside on a single computing device or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

The embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user." It should be appreciated that a "user" need not be a single individual, and that in some embodiments, actions attributable to a "user" may be performed by a team of individuals and/or an individual in combination with computer-assisted tools or other mechanisms.

EXAMPLE

Providing Symptom Relief and Logging for Hot Flashes

Because the severity of menopausal hot flashes can be linked to lifestyle factors (stress, alcohol, diet), logging hot flashes may allow women experiencing menopause, or other individuals with conditions that experience thermal dysregulation, to better understand the factors in their life that are contributing to increased perceived hot flash intensity. Furthermore, an accurate record of the occurrence of hot flashes may be instrumental for enabling a doctor to best determine the type of treatment best suited for an individual. Currently, sternal skin conductance is considered to be a validated physiological measure of hot flashes. However, in some studies up to one quarter of reported hot flashes resulted in no measured increase in skin conductance. Furthermore, the magnitude of change in sternal skin conductance has little correlation with the perceived intensity of the hot flash. Therefore, doctors still recommend that patients keep manually entered hot flash diaries to provide a systematic approach for collecting subjective data related to a person experiencing hot flashes as a symptom of menopause. However, these manual diaries are prone to over or under reporting due to a variety of factors that complicate self-reporting.

In contrast to the above, a haptic actuator may be used to provide cooling relief for hot flashes experienced by a user. Since cooling sensations are a typically recommended method of providing symptom relief for hot flashes, such a device fits into currently recommended therapies. However, unlike prior therapies, the haptic actuator may also be used to monitor the occurrence and severity of hot flashes in addition to providing symptom relief. For example, the haptic actuator may record a timestamp of each cooling session, a duration of each cooling session, a selected intensity for each cooling session, and a number of cooling sessions in a day. This information may be recorded on the on-board memory of the haptic actuator, an associated computing device, and/a remotely located database to provide a comprehensive log of hot flashes experienced by a particular user. The information included in this record may either be processed by the haptic actuator itself, an associated computing device, and/or may be done remotely to provide quantitative information that acts as a behavioral record of the wearer's vasomotor symptoms. This information may then presented to the user, and/or an associated medical practitioner, as a tool for symptom characterization and management.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A method of operating a haptic actuator, the method comprising:
   activating the haptic actuator multiple times to provide thermal and/or physical sensations to a user to provide symptom relief as perceived by the user for a thermal dysregulation condition of the user, wherein the haptic actuator includes a thermoelectric material configured to be worn on the user, wherein the thermal and/or physical sensations include at least one thermal pulse applied by the thermoelectric material, wherein the at least one thermal pulse has one or more operating parameters;
   confirming that an activation of the multiple activations of the haptic actuator was associated with the thermal dysregulation condition; and
   upon confirming the activation of the haptic actuator was associated with the thermal dysregulation condition, recording information related to the activation of the haptic actuator to create an event log associated with the thermal dysregulation condition, wherein the information includes at least a timestamp of the activation of the haptic actuator, and wherein the information further includes the one or more operating parameters of the at least one thermal pulse.

2. The method of claim 1, further comprising updating the one or more operating parameters of the at least one thermal pulse during symptom relief in response to input from the user to provide a desired amount of symptom relief.

3. The method of claim 2, wherein the information includes the updated one or more operating parameters of the at least one thermal pulse.

4. The method of claim 2, wherein the information includes the one or more operating parameters of the at least one thermal pulse before being updated.

5. The method of claim 1, wherein the information includes one or more physiological states of the user.

6. The method of claim 1, further comprising transmitting the information to a remotely located database that includes the event log associated with the thermal dysregulation condition of the user.

7. The method of claim 1, wherein recording the information includes recording the information in a local memory of the haptic actuator.

8. The method of claim 1, wherein the thermal dysregulation condition is hot flashes.

9. A haptic actuator comprising:
   one or more thermal and/or physical actuators configured to apply thermal and/or physical stimulation to a user, wherein the haptic actuator includes a thermoelectric material configured to be worn on a body of the user; and
   a controller operatively coupled to the one or more thermal and/or physical actuators, wherein the controller is configured to:
      activate the one or more thermal and/or physical actuators multiple times to provide thermal and/or physical sensations to the user to provide symptom relief as perceived by the user for a thermal dysregulation condition of the user, wherein the thermal and/or physical sensations include at least one thermal pulse applied by the thermoelectric material, wherein the at least one thermal pulse has one or more operating parameters;
      confirming that an activation of the multiple activations of the haptic actuator was associated with the thermal dysregulation condition; and
      upon confirming the activation of the haptic actuator was associated with the thermal dysregulation condition, record information related to the activation of the haptic actuator to create an event log associated with the thermal dysregulation condition, wherein the information includes at least a timestamp of the activation of the haptic actuator, and wherein the information further includes the one or more operating parameters of the at least one thermal pulse.

10. The haptic actuator of claim 9, wherein the controller is configured to update the one or more operating parameters of the at least one thermal pulse during symptom relief in response to input from the user to provide a desired amount of symptom relief.

11. The haptic actuator of claim 10, wherein the information includes the updated one or more operating parameters of the at least one thermal pulse.

12. The haptic actuator of claim 10, wherein the information includes the one or more operating parameters of the at least one thermal pulse before being updated.

13. The haptic actuator of claim 9, wherein the information includes one or more physiological states of the user.

14. The haptic actuator of claim 9, wherein the controller is configured to transmit the information to a remotely located database that includes the event log associated with the thermal dysregulation condition of the user.

15. The haptic actuator of claim 9, wherein the controller is configured to record the information in a local memory of the haptic actuator.

16. The haptic actuator of claim 9, wherein the thermal dysregulation condition is hot flashes.

17. The method of claim 1, wherein an activation of the multiple activations of the haptic actuator occurs upon determining an episode of the thermal dysregulation condition is occurring, wherein determining the episode of the thermal dysregulation condition is occurring comprises:
  detecting one or more physiological states of the user based on one or more autonomic physiological inputs, wherein the one or more autonomic physiological inputs include at least one selected from the group of heart rate, skin conductance, skin temperature, blood pressure, and respiratory rate, wherein the one or more autonomic physiological inputs are measured by a sensor configured to be worn on a body of the user; and
  comparing the one or more physiological states of the user to one or more predetermined activation parameters to determine if the episode of the thermal dysregulation condition of the user is occurring.

18. The method of claim 1, wherein the information includes sensor information from a sensor of the haptic actuator, wherein the sensor and the thermoelectric material are disposed in a housing configured to be worn on the user.

19. The haptic actuator of claim 9, wherein the activation of the multiple activations of the haptic actuator occurs upon determining an episode of the thermal dysregulation condition is occurring, wherein determining the episode of the thermal dysregulation condition is occurring comprises:
  detecting one or more physiological states of the user based on one or more autonomic physiological inputs, wherein the one or more autonomic physiological inputs include at least one selected from the group of heart rate, skin conductance, skin temperature, blood pressure, and respiratory rate, wherein the one or more autonomic physiological inputs are measured by a sensor configured to be worn on the body of the user; and
  comparing the one or more physiological states of the user to one or more predetermined activation parameters to determine if the episode of the thermal dysregulation condition of the user is occurring.

20. The haptic actuator of claim 9, further comprising a sensor, wherein the sensor and the thermoelectric material are disposed in a housing configured to be worn on the user, and wherein the information includes sensor information from the sensor.

* * * * *